US010064774B2

(12) United States Patent
Onoda

(10) Patent No.: US 10,064,774 B2
(45) Date of Patent: Sep. 4, 2018

(54) DROP-TYPE AUTOMATIC EXCREMENT PROCESSING DEVICE

(71) Applicant: Kouboh Risyo Co., Ltd., Hitachiomiya-shi, Ibaraki (JP)

(72) Inventor: Toshimitsu Onoda, Hitachiomiya (JP)

(73) Assignee: Kouboh Risyo Co., Ltd., Hitachiomiya-shi (JP)

( * ) Notice: Subject to any disclaimer, the term of this patent is extended or adjusted under 35 U.S.C. 154(b) by 324 days.

(21) Appl. No.: 14/894,095

(22) PCT Filed: Jul. 16, 2013

(86) PCT No.: PCT/JP2013/069235
§ 371 (c)(1),
(2) Date: Nov. 25, 2015

(87) PCT Pub. No.: WO2015/008319
PCT Pub. Date: Jan. 22, 2015

(65) Prior Publication Data
US 2016/0101007 A1 Apr. 14, 2016

(51) Int. Cl.
*A61F 5/451* (2006.01)
*A61G 9/00* (2006.01)
(Continued)

(52) U.S. Cl.
CPC ............... *A61G 9/00* (2013.01); *A61F 5/451* (2013.01); *A61G 7/005* (2013.01); *A61G 7/02* (2013.01)

(58) Field of Classification Search
CPC .............. A61F 5/451; A61G 7/02; A61G 9/00
(Continued)

(56) References Cited

U.S. PATENT DOCUMENTS 4,281,655 A * 8/1981 Terauchi ............... A61F 5/451
4/305
4,677,700 A * 7/1987 Su ........................ A61G 7/02
4/420.4
(Continued)

FOREIGN PATENT DOCUMENTS

JP 62-19179 B2 4/1987
JP 4-105650 A 4/1992
(Continued)

OTHER PUBLICATIONS

International Search Report (PCT/ISA/210) issued in PCT Application No. PCT/JP2013/069235 dated Oct. 29, 2013, with English translation (four (4) pages).
(Continued)

*Primary Examiner* — Susan Su
(74) *Attorney, Agent, or Firm* — Crowell & Moring LLP

(57) ABSTRACT

The present invention pertains to a drop-type automatic excrement processing device configured so that the degree of restraint on the body of the objective person to whom the device is fitted is made less. The device comprises the following: a diaper cover 1 that covers the buttocks and loins of a objective person for use such as an aged person; a feces receiver 2 and a urine catching pad 3 which are fitted to the diaper cover 1; a feces and urine intake pipe 5 for receiving feces or urine discharged through the feces receiver 2 and guiding the received matter into a wastes container 4; a valve unit 6 interposed in the intermediate part of the intake pipe 5; a washing-water tank 7 for storing washing water for washing the buttocks and the like; a warm wind generating means 8 for generating a warm wind used for drying the buttocks and the like after washing; and a control means 9 for controlling the operation of each of the foregoing. The device is characterized in that a defecation tube 2b of the feces receiver 2 protruding from the diaper cover 1 projects
(Continued)

below a bed 10 through a defecation hole 10*h* provided in the bed 10 and is connected to a funnel-shaped part 5*a* of the upper part of the feces and urine intake pipe 5 so as to be vertically movable and inclinable.

3 Claims, 11 Drawing Sheets

(51) Int. Cl.
    *A61G 7/005* (2006.01)
    *A61G 7/02* (2006.01)

(58) Field of Classification Search
    USPC ...................................................... 4/449–486
    See application file for complete search history.

(56) References Cited

U.S. PATENT DOCUMENTS

| | | | |
|---|---|---|---|
| 5,342,583 A * | 8/1994 | Son ......................... | A61F 5/451 2/84 |
| 6,167,578 B1 * | 1/2001 | Kitamura ................ | A61F 13/42 4/443 |
| 6,443,939 B1 * | 9/2002 | Oki ......................... | A61F 5/451 4/484 |
| 6,651,267 B1 * | 11/2003 | Utz ......................... | A61G 7/02 4/443 |
| 2002/0010446 A1 * | 1/2002 | Maimets ................. | A61F 5/451 604/355 |
| 2006/0084932 A1 * | 4/2006 | Koizumi ................. | A61F 5/451 604/319 |
| 2011/0308017 A1 * | 12/2011 | Nakamura ............... | A61G 7/02 5/605 |
| 2016/0331599 A1 * | 11/2016 | Saitoh ..................... | A61G 9/00 |

FOREIGN PATENT DOCUMENTS

| | | |
|---|---|---|
| JP | 8-289906 A | 11/1996 |
| JP | 10-85275 A | 4/1998 |
| JP | 3077083 B2 | 8/2000 |
| JP | 3113401 U | 9/2005 |
| JP | 3129272 U | 2/2007 |

OTHER PUBLICATIONS

Japanese-language Written Opinion (PCT/ISA/237) issued in PCT Application No. PCT/JP2013/069235 dated Oct. 29, 2013 (three (3) pages).

International Preliminary Report on Patentability ((PCT/IB/326 and PCT/IB/373) issued in PCT Application No. PCT/JP2013/069235 dated Jan. 28, 2016, including English translation of document C2 (Japanese-language Written Opinion (PCT/ISA/237)) previously filed on Nov. 25, 2015 (Six (6) pages).

\* cited by examiner

DROP-TYPE AUTOMATIC EXCREMENT PROCESSING DEVICE

TECHNICAL FIELD

The present invention relates to a drop-type automatic excrement processing device. The device automatically processes feces or urine discharged from a bedridden aged or sick person and maintains the buttocks and loins of such person, who uses the device, cleanly.

BACKGROUND ART

There are various ideas for excrement processing devices of this kind. A device of this kind generally includes: a diaper-like material that wraps lumber and buttocks of human body, a washing-water feeding means connected to the diaper-like material, an exhaust means connected to the diaper-like material for exhausting the washing-water and wastes, a detection means for detecting discharged feces and urine, and a control means for controlling working of the washing-water feeding means and a drying air blowing means, based on the detection results of defecation and urination obtained by the detection means.

The device of that kind has problems in assuring the close fitting of the diaper-like material to the human body, detecting discharged feces and urine definitely, washing and exhausting feces and urine reliably, making the applying and removing of the device to and from the human body be easy, and ensuring the freedom of the motion of aged or sick person who wears the device on corresponding part of the body, and other similar problems. Patent literatures 1 and 2 have provided ideas to solve these problems.

For example, the art described in Patent literature 1 uses a swimming ring-like item. This item is placed underneath the human body, particularly between the diaper-like material and a feces receiver, to assure a close-fitting of the device to the human body. Further, the internal pressure of the swimming ring-like item is increased during feces processing to prevent the spilling of the washing-water and wastes from the verge of the device.

The art described in Patent literature 2 simplifies the handling of the device in applying and removing to and from the human body by bundling the ancillaries into one hose unit, the ancillaries including hoses of means for feeding and discharging washing-water, and wires and cables for transmission of signal from a detection means to permit mounting and dismounting them as one hose unit. Further, this art makes the diaper-like material have a bellow-like flexible construction to prevent leakage of the washing-water.

Moreover in Patent literatures 1 and 2, the feces-conveying pipe and hoses such as a filth suction hose extend out to the main unit of the device from the bed flank. This configuration is onerous for an objective person who wears the device, and is, further, an obstruction for a care-giving person. In addition to these, there is a risk of arising a problem such that the hoses may partly squash attributable to the hose's possible entering under the objective person wearing the device.

The art defined in Patent literature 3 is an excrement treating device that is invented by the inventor of the present invention. The discharge pipe that couples the bedpan and the filth container is pendent downward through a hole opened in a bed. The lower end of the discharge pipe extends to reach the filth container. A part of the pipe positions at a lower part of the body of wearer, as described in Patent literatures 1 and 2. Therefore, there is no room to happen such a problem that a part of the pipe may squash. Further, the discharge pipe has a flexible joint in its middle. Although the flexible joint permits bending in the direction of front and back, and right and left, but expansion and contraction is not possible; a longitudinal behavior has no freedom. Because of this, the bedpan wearer encounters a restraint problem in that point.

LITERATURE OF RELATED ART

Patent Literature

{Patent Literature 1} Japanese Examined Patent Publication No. 1987-19179
{Patent Literature 2} Japanese Patent No. 3077083
{Patent Literature 3} Japanese Utility Model No. 3129272

SUMMARY OF THE INVENTION

Problems to be Solved by the Invention

An object of the present invention is to provide a drop-type automatic excrement processing device that is easy to apply to the desired part of a body, the device laying a lowered degree of restraint on the body of an objective person on bed who wears the device with a certain degree of freedom for moving the body ensured, while having the advantages of existing excrement processing unit as well.

Means for Solving the Problem

The first aspect of the present invention is a drop-type automatic excrement processing device, comprising:
a diaper cover having an opening for defecation and urination roughly in the buttocks-corresponding position;
a feces receiver comprising a belt-shaped rubber sheet part to be arranged inside the diaper cover, the belt-shaped rubber sheet part one end of which being circular having a circular opening, a defecation tube the opening edge of the top end of which being fixedly jointed to the opening edge of the circular opening of the circular end of the belt-shaped rubber sheet part, a blower tube communicating with upper-inside area of the defecation tube, and a water pipe inserted in the intermediate part of the blower tube, the top end of the water pipe protruding toward the belt-shaped rubber sheet part from the defecation tube;
a disposable urine catching pad arranged between the belt-shaped rubber sheet part of the feces receiver and the inside of the diaper cover in such a state that the defecation tube is inserted in the opening for defecation and urination of the diaper cover from the inside thereof and the belt-shaped rubber sheet part is arranged on the lower part of the inside of the diaper cover;
a feces and urine intake pipe, the bottom end of which being connected to a wastes container, the feces and urine intake pipe being adaptable to insertion of the defecation tube of the feces receiver in a funnel-shaped part which is the upper part of the feces and urine intake pipe, the insertion being performed in a manner that allows a slant-insertion and a free movement in raising and lowering, the defecation tube being pendent downward below a bed through the opening of the defecation hole in the bed on which a user of the device lies, the funnel-shaped part being fitted on the undersurface of the bed;
a valve unit inserted in the intermediate part of the feces and urine intake pipe, the valve unit being opened detecting the occurrence of defecation and urination based on the weight or pressure caused from the reception, by the valve unit, of the feces or urine falling from the device-wearer and washing-water drainage or exhaust air;

a washing-water tank connected to the water pipe through a pump unit, the washing-water tank having a warming unit;

a warm wind generating means connected to the blower tube; and a control means that controls the pump unit and the warm wind generating means so that, when the valve unit opens while the pump unit or the warm wind generating means is not operating, the pump unit feeds a predetermined quantity of warm washing-water into the water pipe after a predetermined time after the opening of the valve unit and the warm wind generating means blows warm wind into the blower tube for a predetermined time, after the water feeding stop.

The second aspect of the present invention is a drop-type automatic excrement processing device according to the first aspect of the present invention, wherein the upper end of the funnel-shaped part of the feces and urine intake pipe is fitted on the undersurface of the bed in a manner that allows relative slanting with respect to the bed so that the funnel-shaped part keeps a horizontal position when the bed is raised.

The third aspect of the present invention is a drop-type automatic excrement processing device according to the first or second aspect of the present invention, wherein the water pipe has a connector at its intermediate part, the connector detachably connecting both ends on the intermediate part of the water pipe, wherein the connector on one side is comprised of a gripping sleeve, an annular magnet positioned inside the gripping sleeve at the place recessed by a predetermined distance from the end of the gripping sleeve, and a hose component, which configures the water pipe, inserted in the annular magnet from its back side so as to penetrate through and to be fixed there; and the connector on the other side is comprised of a gripping sleeve, a reversed polarity annular magnet positioned inside the gripping sleeve protruding by a predetermined distance from the end thereof, and a hose component, which configures the water pipe, inserted in the reversed polarity annular magnet from its back side to the position recessed by the distance equal to the penetration distance of the hose component in the connector on one side from the end of the reversed polarity annular magnet.

Advantageous Effect of the Invention

The drop-type automatic excrement processing device of the first aspect of the present invention is used for a bedridden aged or sick person such as an abasic person and is able to process feces and urine of such person automatically and sanitarily.

The setting of the drop-type automatic excrement processing device of the first aspect of the present invention is completed by putting the diaper cover having the feces receiver and the urine catching pad on the crotch of the objective person, and placing the related units and components of the device on the undersurface of or below the bed. Putting the diaper cover having the feces receiver and the urine catching pad on the objective person is performed in the steps of: inserting the diaper cover underneath the buttocks of the objective person who is to wear the item, inserting the defecation tube protruding from the diaper cover in the defecation hole opening in the bed, folding back a bottom flap of the diaper cover to the underbelly side of the objective person through the crotch, folding back the wrapping flaps on both sides of the diaper cover from its lateral sides toward the underbelly side and fastening each of flaps mutually by a hook-and-loop fastener, and fastening the wrapping flaps by a hook-and loop fastener also to the bottom flap having been folded through the crotch already.

In the diaper cover put on the objective person, as stated above, the defecation tube of the feces receiver, the defecation tube protruding from the opening for defecation and urination opening roughly in the buttocks-corresponding position, is inserted in the defecation hole in the bed. This brings the defecation tube to a state of having been inserted in the funnel-shaped part of the feces and urine intake pipe fitted in advance on the undersurface of the bed at the position corresponding to the defecation hole in a manner that allows a free relative movement in raising and lowering and in a slant direction. Putting the diaper cover on the objective person as stated above completes the setup of the device.

In addition, those components listed below are to be installed in advance on the undersurface of or below the bed together with the feces and urine intake pipe. The components include: the wastes container to which the bottom end of the feces and urine intake pipe is connected, the warm wind generating means that blows warm wind through the blower tube connected to the upper part of the defecation tube, the washing-water tank for feeding warm washing-water in the water pipe that extends from the intermediate part of the blow tube to the immediate-below the buttocks of the device-wearer through the defection tube, the washing-water tank having the warming unit, and the control means.

The drop-type automatic excrement processing device by the first aspect of the present invention works as follows. When the wearer of the device urinates or defecates, the urine or feces falls, passing through the defecation tube of the feces receiver, into the funnel-shaped part of the upper part of the feces and urine intake pipe. The discharged matter slips down to the valve unit provided on the intermediate part of the feces and urine intake pipe; the weight of the matter causes the valve to open, then the matter further falls into the wastes container. The valve being opened indicates that the occurrence of defecation or urination is detected. After a predetermined time from the detection of the occurrence of the defecation or urination, the pump unit pumps warm washing-water warmed in the washing-water tank and sends into the water pipe. The washing-water thus sent to the water pipe washes around the buttocks of the device-wearer and then flows down into the wastes container through the defecation tube, feces and urine intake pipe, and the valve unit provided on the intermediate part of the feces and urine intake pipe as with the feces.

After the completion of the sending the predetermined quantity of the warm washing-water, the warm wind generating means operates to blow the warm wind around the buttocks through the blower tube to dry the area around the buttocks after the washing. The warm wind for drying goes to the wastes container travelling through the same path as with the feces or urine and then the wind is exhausted from the wastes container with the bad smell component removed. The wastes container is to have an exhaust means that exhaust the air or gas in the tank through a filter. Thus, the area around buttocks of the aged or a sick person, who wears the diaper cover of the device prepared in the above-stated conditions, is cleaned immediately after the defecation or urination with filth thereon removed. Accordingly, the area around the buttocks is maintained sanitarily always.

In addition, the device has no fixed direct connection between the defecation tube of the feces receiver and the feces and urine intake pipe, that is, the lower part of the defecation tube is in an inserted state in the funnel-shaped part of the upper part of the feces and urine intake pipe in a manner that allows a free movement in raising and lowering and a slant-insertion. Therefore, the bedridden aged or a sick person who wears the diaper cover having the feces receiver and the urine catching pad does not have an excessive restraint on bodily movement. Accordingly, the device has an advantage in that such person can maintain a relaxed position.

The drop-type automatic excrement processing device by the second aspect of the present invention works as follows. When the bed is raised to change the position of the aged or a sick person on bed, the top end of the funnel-shaped part of the upper part of the feces and urine intake pipe can always maintain horizontal. Consequently, this configuration does not adversely affect the coupling state with the wastes container located in the lowermost position of the device setup.

The drop-type automatic excrement processing device by the third aspect of the present invention offers advantages as follows. Coupling the connector on one side with the connector on the other side is easily and reliably performable for anyone. This eases the cleaning and replacement of the washing-water tank. Further, the use of a magnet brings about another advantage in that the warm washing-water that flows through the magnet undergoes magnetizing treatment.

BRIEF DESCRIPTION OF THE DRAWINGS

FIG. 3 This is a schematic plan view.

FIG. 9 This illustrates the funnel-shaped part of the feces and urine intake pipe in the embodiment.

FIG. 11 This is a cross-sectional view.

MODE OF IMPLEMENTING THE INVENTION

Figure 1:
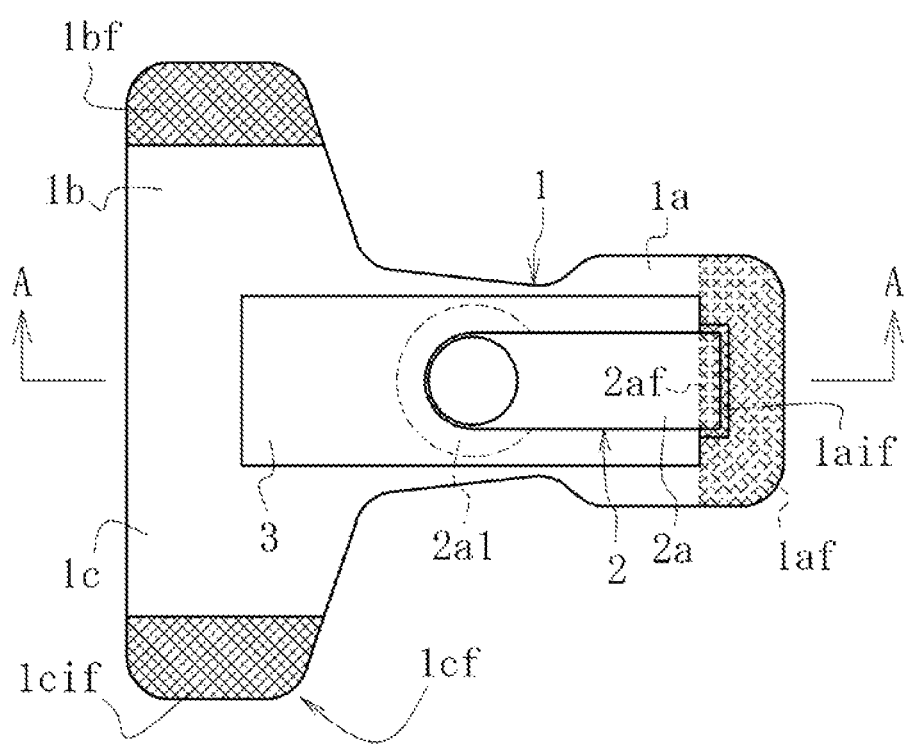
FIG. 1 This is a schematic plan view of the diaper cover in an embodiment of the drop-type automatic excrement processing device in the state that the feces receiver and the urine catching pad are fitted inside the diaper cover.

The following describes modes of implementing the invention based on an embodiment.

The drop-type automatic excrement processing device in this embodiment, as shown in FIGS. 1, 2, 3, and 8, comprises:

a diaper cover 1 that covers the buttocks and loins of an objective person such as an aged person;

a feces receiver 2 and a urine catching pad 3 that are fitted on the diaper cover 1;

a feces and urine intake pipe 5 that takes in the feces and urine discharged from the objective person such as an aged person through the feces receiver 2 and sends such matter to a waste tank 4;

a valve unit 6 inserted in the intermediate part of the feces and urine intake pipe 5;

a washing-water tank 7 that keeps warm washing-water for washing the buttocks;

a warm wind generating means 8 that generates warm wind for drying the buttocks after washing; and a control means 9 for controlling working of each unit.

Figure 2:
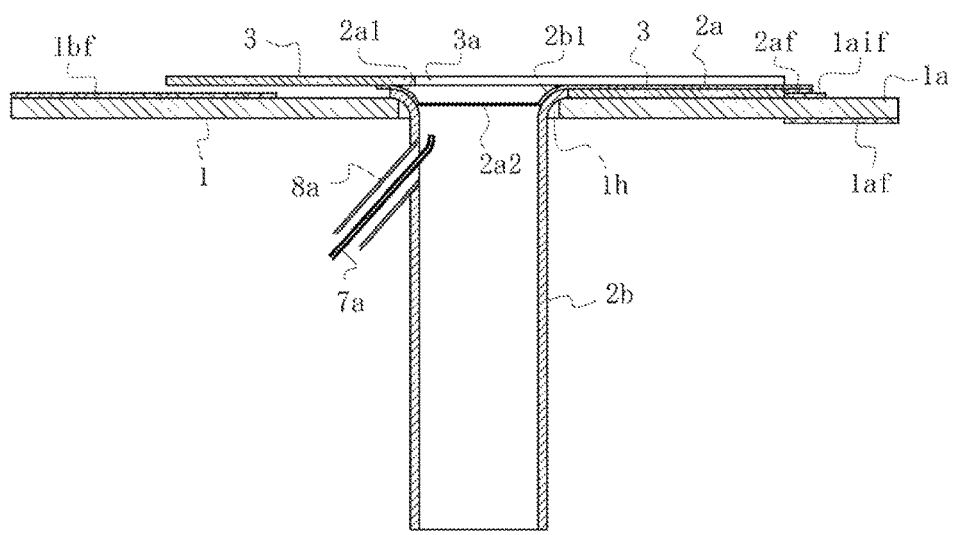
FIG. 2 This is an enlarged cross-sectional view of the diaper cover sectioned along the line A-A in the FIG. 1.
Figure 3A:
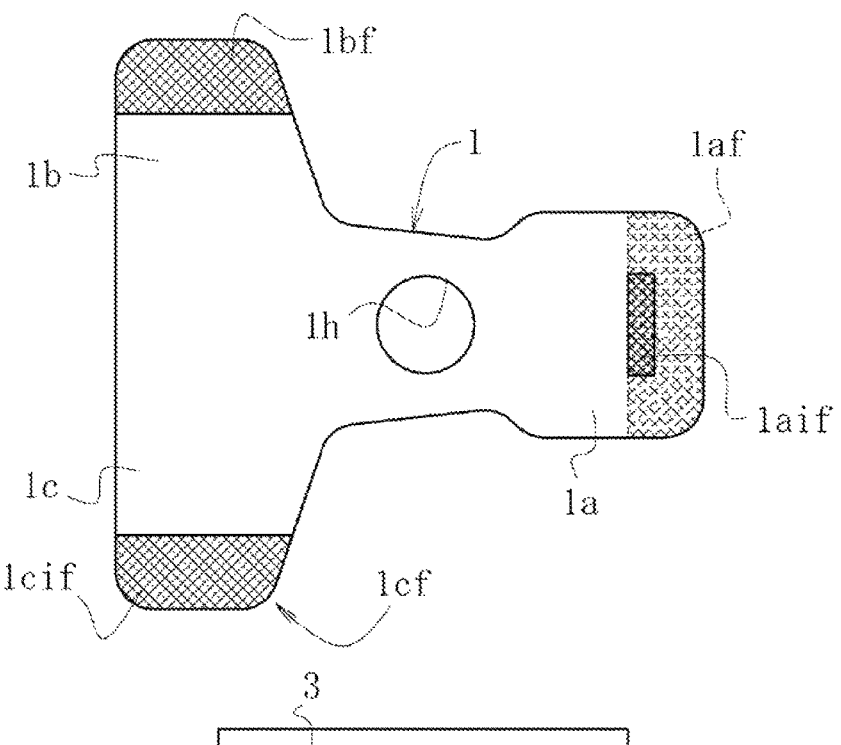
FIG. 3A: A schematic plan view of the diaper cover of the embodiment of the drop-type automatic excrement processing device.

The diaper cover 1 has a similar configuration to an existing one, particularly as shown in FIGS. 1, 2, and 3(a), except that it has an opening for defecation and urination 1h roughly in its center. The diaper cover 1 has a bottom flap 1a that extends downward from the area roughly the center of the opening for defecation and urination 1h and a prolonged portion that extends upward from the area roughly that center and a pair of wrapping flaps 1b and 1c each of which spreads toward the right side and the left side from that prolonged portion. The end of the bottom flap 1a has a hook-and-loop fastener 1af on its outer surface and a hook-and-loop fastener 1aif on its inner surface. The wrapping flap 1b (the flap on the right side) has a hook-and-loop fastener 1bf on its inner surface and the wrapping flap 1c (the flap on the left side) has a hook-and-loop fastener 1cf on its outer surface; the wrapping flap 1c further has a hook-and-loop fastener 1cif on its inner surface. The hook-and-loop fastener 1bf on the inner surface of the wrapping flap 1b on the right side and the hook-and-loop fastener 1cif on the inner surface of the wrapping flap 1c on the left side are male fasteners. The hook-and-loop fastener 1cf on the outer surface of the wrapping flap 1c on the left side and the hook-and-loop fastener 1af on the outer surface of the bottom flap 1a are female fasteners.

Further, the diaper cover 1 is made of a plastic film that has a required strength and is impermeable to water.

The feces receiver 2, as shown in FIGS. 1, 2, 3(c), and 4, comprises:

a belt-shaped rubber sheet part 2a that is arranged in a jointed state on the inner surface of the diaper cover 1;

a defecation tube 2b made of plastic fitted on one end of the belt-shaped rubber sheet part 2a perpendicularly thereto;

a blower tube 8a that communicates with the upper part of the defection tube 2b; and a water pipe 7a that is inserted in the upper-intermediate part of the blast tube 8a.

Figure 3B:
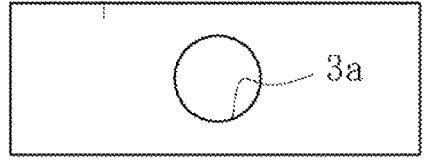
FIG. 3B: A schematic plan view of the urine catching pad.
Figure 3C:
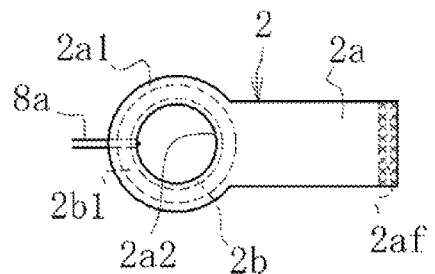
FIG. 3C: A schematic plan view of the feces receiver.
Figure 4:
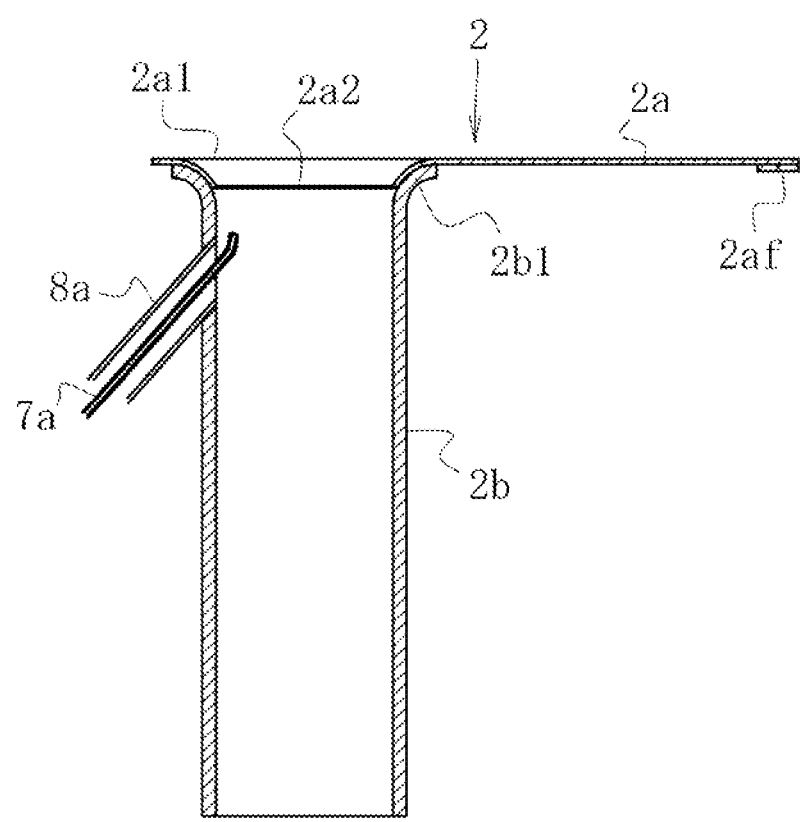
FIG. 4 This is a schematic cross-sectional view of the feces receiver of the embodiment of the drop-type automatic excrement processing device.

As shown in FIGS. 1 and 3(c), one end of the belt-shaped rubber sheet part 2a forms a round end 2a1 having a diameter larger than the width of other part thereof. The round end 2a1 has a circular opening 2a2 concentrically therein having an inner diameter approximately same as the inner diameter of the defecation tube 2b. On the undersurface of the other end of the belt-shaped rubber sheet part 2, a male hook-and-loop fastener 2af is arranged, wherein the faster is to engage with the hook-and-loop fastener 1aif on the inner surface of the bottom flap 1a of the diaper cover 1. The defecation tube 2b joins with the belt-shaped rubber sheet part 2a at the round end 2a1 of approximate-circular shape. Particularly, as shown in FIGS. 2, 3, and 4, the uppermost end of the opening edge of the defecation tube 2b, which is originally a straight cylindrical member, forms a gradual bell-mouth shape. On an opening edge 2b1 of this gradual bell-mouth shaped part, the opening edge of the round end 2a1 of the belt-shaped rubber sheet part 2a is put, and then, they are fixedly joined aligning the axes of the circular opening 2a2 of the round end 2a1 and the defection tube 2b. In this embodiment, this joining is performed using glue.

Figure 8:
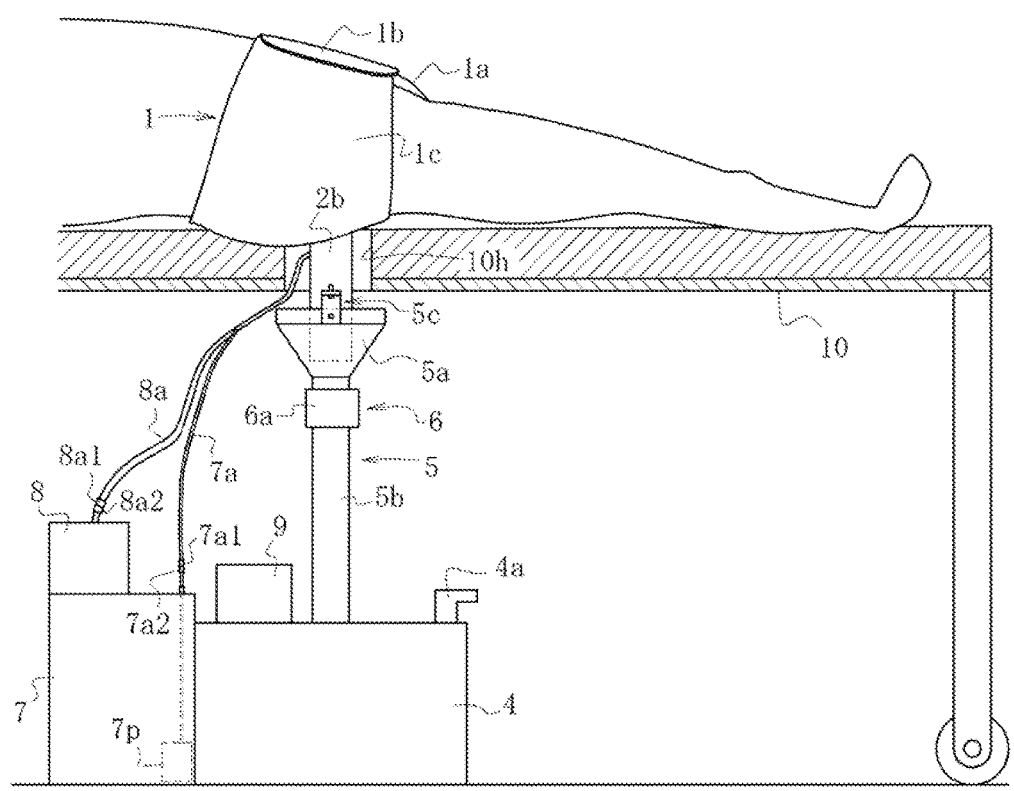
FIG. 8 This is an explanatory side view schematically illustrating the embodiment of the drop-type automatic excrement processing device set on a bed.

The blower tube 8a is, as shown in FIGS. 2, 3(c), and 4, a hose component the upper end of which is connected to the upper-intermediate part of the defecation tube 2b. The bottom end of the blower tube 8a is connected to the warm wind generating means 8 as shown in FIG. 8. As shown in that figure, the blower tube 8a has a pair of male-female detachable connectors 8a1 and 8a2 in its intermediate part. Thereby, the blower tube 8a can be detached from the warm wind generating means 8 depending on the necessity. Particularly, as shown in FIGS. 2 and 4, the jointing between the blower tube 8a and the defecation tube 2b is formed in a configuration as follows: The blower tube 8a is jointed to the defecation tube 2b in an upward-slant direction so that the upper end thereof opens toward the upper end of the defecation tube 2b.

The water pipe 7a is a hose component having a diameter smaller the blower tube 8a. As shown in FIGS. 2, 4, 7, and 8, the upper part of the water pipe 7a is inserted in the upper-intermediate part of the blower tube 8a. The distal end of the upper part of the water pipe 7a so inserted protrudes to the inside of the defecation tube 2b from the top end of the blower tube 8a, being oriented toward the upper end of the defecation tube 2b. Particularly, as shown in FIG. 8, the bottom end of the water pipe 7a is connected to a pump unit 7p accommodated in the washing-water tank 7. The pump unit 7p pumps the warm washing-water in the washing-water tank 7 to feed to the buttocks in the diaper cover 1. Thus, the water pipe 7a forms a washing-water feeding path to the buttocks in the diaper cover 1. In the intermediate part of the water pipe 7a, the detachable connectors, a connector 7a1 on one side and a connector 7a2 on the other side, are inserted. The water pipe 7a is separable from the washing-water tank 7 by releasing the connection between the connector 7a1 on one side and the connector 7a2 on the other side.

Figure 11A:
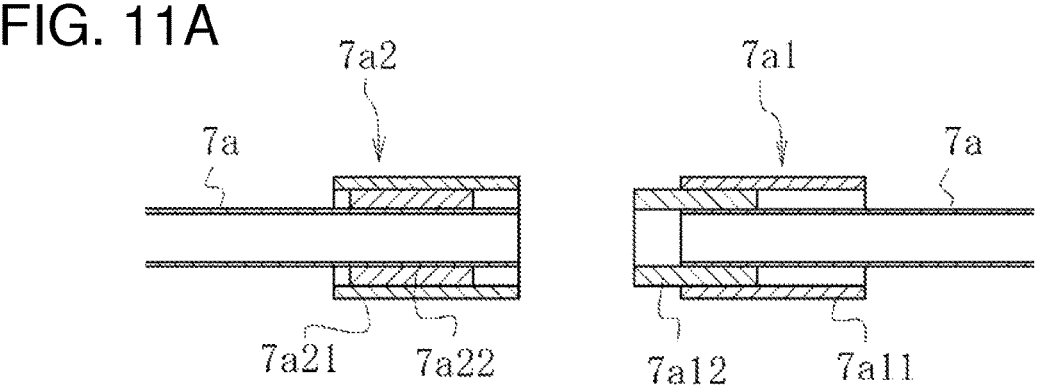
FIG. 11A: A separation state of the connector to be inserted in the intermediate part of the water pipe, the connector on one side and the connector on the other side being disconnected.
Figure 11B:
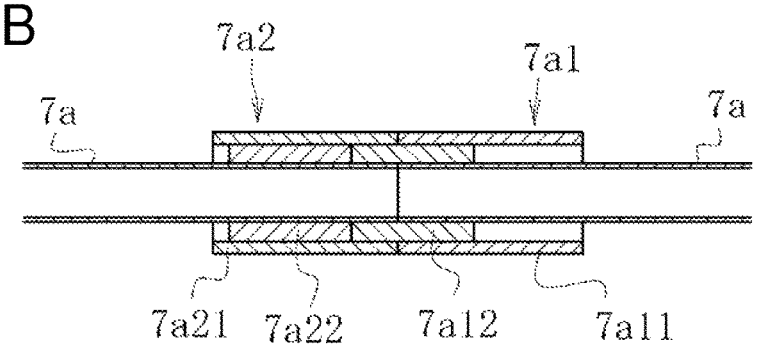
FIG. 11B: A state in which the connection is established.

The connector 7a1 on one side is the connector attached on the bottom end of the upper part of the water pipe 7a, which is shown in the right side portion of FIGS. 11(a) and 11(b). As shown in those figures, the connector 7a1 on one side comprises: a gripping sleeve 7a11 of plastic, an annular magnet 7a12 positioned inside the gripping sleeve 7a11 protruding by a predetermined distance from the end thereof, and the upper part of the water pipe 7a inserted in the annular magnet 7a12 from its back side to its middle point.

The connector 7a2 on the other end is the connector shown in the left side portion of FIGS. 11(a) and 11(b). This connector comprises: a gripping sleeve 7a21 of plastic; a reversed polarity annular magnet 7a22 positioned inside the gripping sleeve 7a21 at the place recessed by a predetermined distance from the end thereof, the polarity of the annular magnet 7a22 being reverse to the polarity of the connector 7a12 on one side; and the lower part of the water pipe 7a inserted in the reversed polarity annular magnet 7a22 from its back side to the position protruding by the distance equal to the recess distance of the lower part of the water pipe 7a in the connector 7a1 on one side so as to be fixed there.

As shown in FIGS. 1 and 3(b), the urine catching pad 3 is a belt-shaped component of a rectangular shape having an opening 3a in the center thereof; the material of this component is exactly equivalent to that in the existing ones. The opening 3a has a size slightly larger than the inner diameter of the defecation tube 2b of the feces receiver 2. The urine catching pad 3 is for absorbing moisture such as urine to prevent the skin of the wearer of the device from bad effects thereof and is a disposable item as with the other ones commonly used.

The wastes container 4 is a container unit that collects feces, urine, and drainage of the washing-water wastes, and the bottom end of the feces and urine intake pipe 5 is connected thereto as shown in FIG. 8. The wastes container 4 has an exhaust port 4a having an adsorbent filter on its upper part for adsorbing bad smell component. The exhaust port 4a prevents bad smell emission during the taking-in the feces, urine, and the washing-water drainage allowing a smooth intake; the port also works as an exhaust opening of the drying air.

The feces and urine intake pipe 5 is comprised of a funnel-shaped part 5a of its upper part and a straight pipe part 5b of its lower part, as shown in FIGS. 7, 8, 9(a), and 9(b). The bottom end of the feces and urine intake pipe 5 is connected communicatively to the upper part of the wastes container 4. In the upper-intermediate part of the straight pipe part 5b, the valve unit 6 is inserted. In a usual state, bad smell from the filth in the wastes container 4 does not spread because the upper and bottom end of the straight pipe part 5b are closed both in their positions. As shown in FIGS. 7, 8, 9(a), and 9(b), the funnel-shaped part 5a has one pair of an L-shaped connection metal fittings 5c on its uppermost peripheral side face and they are arranged at an interval of 180-degree; using this metal fittings, the funnel-shaped part 5a can be joined to the predetermined place on the bed.

Figure 9A:
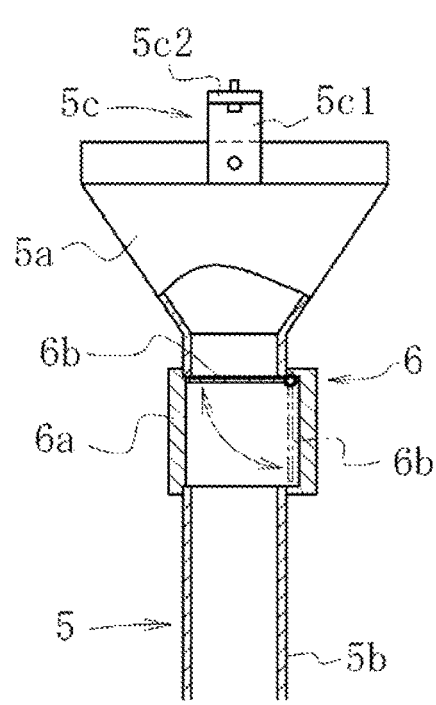
FIG. 9A: A schematic partially sectioned side view around the funnel part.
Figure 9B:
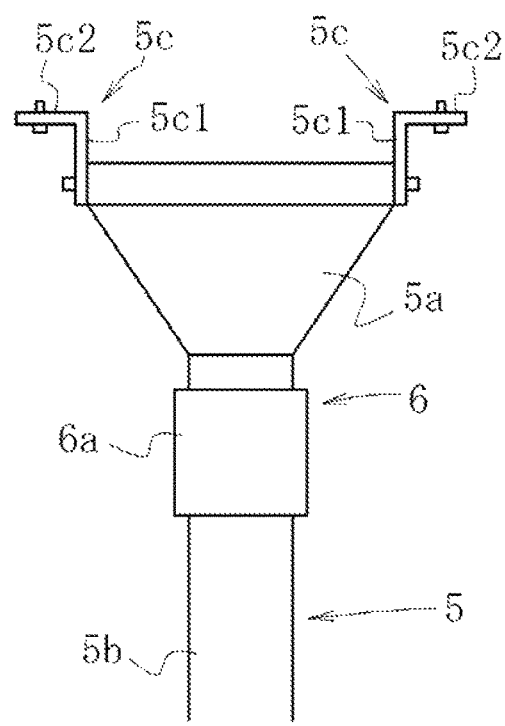
FIG. 9B: A schematic front view.
Figure 10:
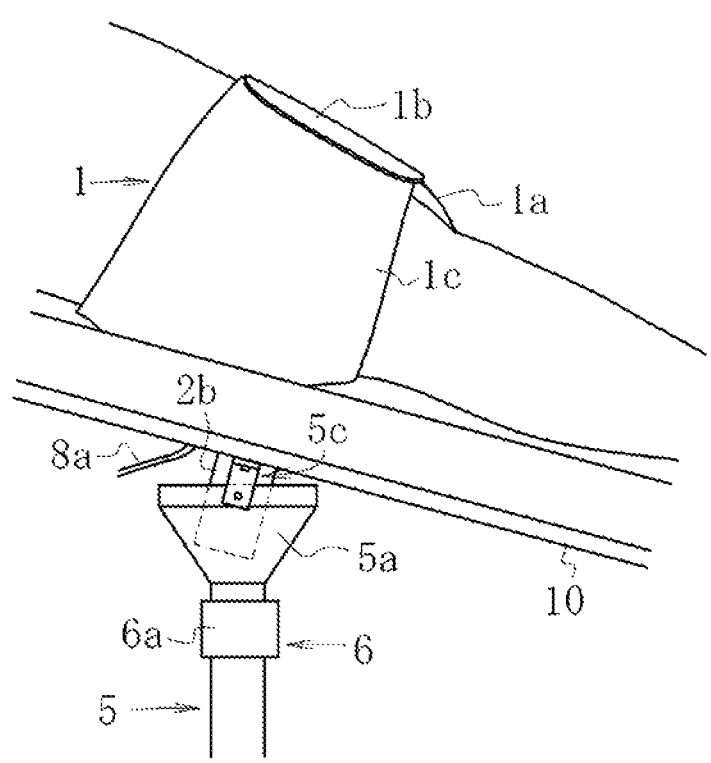
FIG. 10 This is an explanatory schematic side view to show the relationship between the bed and the funnel-shaped part of the feces and urine intake pipe when the bed is raised for the position change.

Particularly, as shown in FIGS. 9(a) and 9(b), each of vertical tongues 5c1 of the L-shaped connection metal fitting 5c are rotatably fitted, using a pin, on the upper peripheral side face of the funnel-shaped part 5a at an interval of 180-degree as stated above. Each of horizontal tongues 5c2 is pin-secured fixedly on the undersurface of a bed 10 as shown in FIG. 10. The funnel-shaped part 5a is fitted on the undersurface of the bed 10 as shown in FIG. 8 approximately aligning its axis with the axis of a defecation hole 10h that opens roughly in the center of the bed 10.

As stated above and shown in FIGS. 7 to 10, the valve unit 6 is a valve mechanism inserted in the upper-intermediate part of the straight pipe part 5*b* of the feces and urine intake pipe 5. As shown in FIG. 9(*a*) particularly, the valve unit 6 basically has a valve box 6*a* that couples communicatively the upper and the lower part of the straight pipe part 5*b* and a plate-like valve member 6*b* each end of which is fitted rotatably to one side of the valve box 6*a*. The valve member 6*b* is usually biased by a biasing means, which is not illustrated in the figures, so that it is oriented in the direction orthogonal to the axis of the straight pipe part 5*b*. The spring constant of the biasing means is set to an extent either: the weight of the feces or the like when a minimum amount of such matter falls on the valve member 6*b* or the pressure of warm wind from the warm wind generating means 8 when the exhaust of drying air flows-in, whichever is smaller for causing the downward rotation of the valve member 6*b*. As the biasing means, this embodiment uses a coil spring that is wound on the rotary shaft on the rotating end of the valve member 6*b*.

On the rotating end of the valve member 6*b*, a detection means, which is not illustrated in the figures, is provided to detect the rotation of the valve member 6*b* when the valve rotates downward to a certain angle, 50-degree or more in this embodiment. A detection signal detected by this detection means is sent to the control means 9 through a wire, which is not illustrated. Receiving the detection signal, the controller 9 judges that the bedridden aged or sick person defecated.

As stated above and shown in FIG. 8, the washing-water tank 7 is a container for storing warm washing-water and accommodates the pump unit 9*p* for sucking the warm washing-water. Further, the tank is equipped with a warming unit, which is not illustrated, for warming the washing-water reserved in the tank. The pump unit 7*p* is connected to the water pipe 7*a*.

As shown in FIG. 8, the warm wind generating means 8 is installed on the washing-water tank 7 in this embodiment and is a means for generating the warm wind to be sent to the buttocks wrapped in the diaper cover 1 through the blower tube 8*a*. Specifically in this embodiment, the warm wind generating means 8 comprises a blower, which is not illustrated, and a heater, which is not illustrated, for heating the wind generated by the blower.

As shown in FIG. 8, the control means 9 is installed on the wastes container 4 in this embodiment. The control means 9 sends a pump-driving signal to the pump unit 7*p* in the washing-water tank 7 after a predetermined time, one minute and 30 seconds in this embodiment, from the reception of the detection signal which the detection means outputs on detection of the defecation by the detection means of the valve unit 6. Thereby, the control means 9 makes the pump unit 7*p* operate a pumping action of feeding 300 cc in 10 seconds. Further, after the pumping action of 10 seconds of the pump unit 7*p* completes, the control unit 9 sends a signal that makes the warm wind generating means 8 operate for two minutes, during which the warm wind is sent out. The warming unit, which is not-illustrated, of the washing-water tank is controlled to operate continuously so as to maintain the washing-water in the washing-water tank 7 at the preset temperature. The warming temperature of the washing-water can be set freely by the administrator of the device.

The bed 10 to which the drop-type automatic excrement processing device in this embodiment is applicable is basically nothing different from those usual beds. However, the bed 10 has the defecation hole 10*h* approximately its center and requires attaching the funnel-shaped part 5*a* of the feces and urine intake pipe 5 on the undersurface thereof at the position corresponding to the defecation hole 10*h* using the L-shaped connection metal fittings 5*c*, as stated above. When a bed satisfies these features and the requirement, the device is settable on such bed.

Thus, when the drop-type automatic excrement processing device in this embodiment is used in a manner as described below, the device exhibits an excellent effect as will be stated later.

The feces receiver 2 and the urine catching pad 3 are fitted on the diaper cover 1 of this device, and then the diaper cover 1 so prepared is put on the buttocks of a bedridden objective aged or sick person lying on the bed 10.

The diaper cover 1 is spread with its inside up as shown in FIG. 3(*a*), and the feces receiver 2 is put thereon as shown in FIG. 1. The feces receiver 2 is prepared in a manner as shown in FIG. 3(*a*), in which the belt-shaped rubber sheet part 2*a* is put on the bottom flap 1*a* of the diaper cover 1, the defecation tube 2*b* is inserted in the opening for defecation and urination 1*h* of the diaper cover 1, to penetrate below the cover, and the urine catching pad 3 is put on the belt-shaped rubber sheet part 2*a* aligning the axis of the opening 3*a* of the urine catching pad 3 and the axis of the defecation tube 2*b* of the feces receiver 2. The preparation steps further continue. The belt-shaped rubber sheet part 2*a* of the feces receiver 2 is drawn out on the urine catching pad 3, through the opening 3*a* of the urine catching pad 3, the belt-shaped rubber sheet part 2*a* is pulled toward outer edge of the bottom flap 1*a* of the diaper cover 1, and then the hook-and-loop fastener 2*af* on the outer surface of the outer edge of the belt-shaped rubber sheet part 2*a* is fastened to the hook-and-loop fastener 1*aif* on the inner surface of the bottom flap 1*a*.

Figure 5:
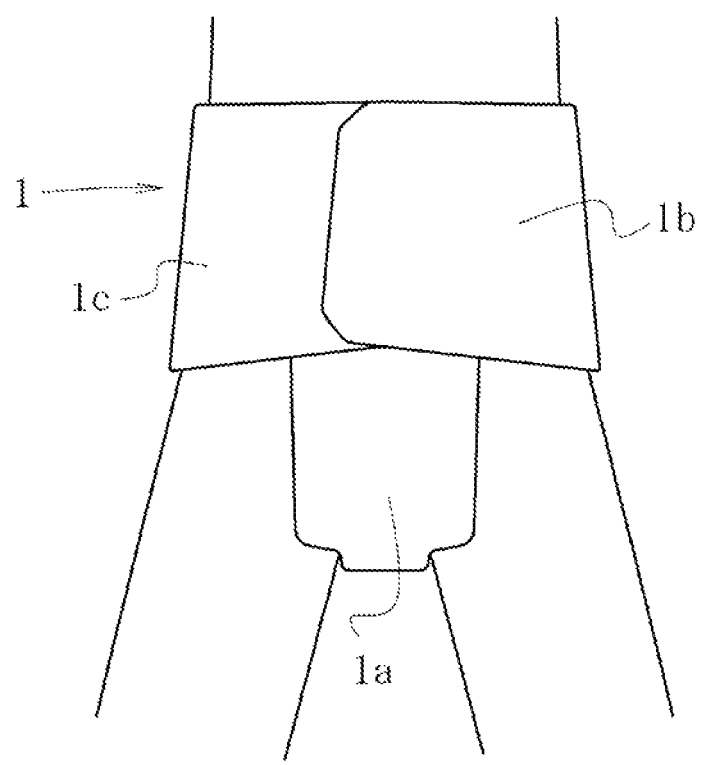
FIG. 5 This is an explanatory plan view schematically illustrating an aged or sick person who is in a state wearing the diaper cover in the embodiment of the drop-type automatic excrement processing device, the feces receiver and the urine catching pad being fitted inside the diaper cover.
Figure 6:
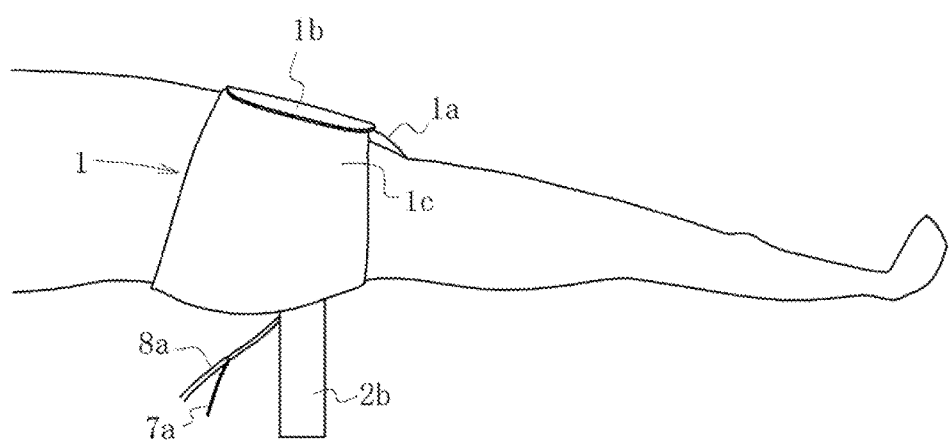
FIG. 6 This is an explanatory side view schematically illustrating an aged or sick person who is in a state wearing the diaper cover in the embodiment of the drop-type automatic excrement processing device, the feces receiver and the urine catching pad being fitted inside the diaper cover.

The diaper cover 1 having the feces receiver 2 and the urine catching pad 3 fitted on its inside in a manner as stated above is put on the buttocks of the bedridden aged or sick person lying on the bed 10 as shown in FIGS. 5 and 6. The diaper cover 1 prepared and spread with its inside up as shown in FIG. 1 is slid under the buttocks of the bedridden aged or sick person, and then the bottom flap 1*a* of the diaper cover 1 is folded back onto the underbelly of the bedridden aged or sick person; further, the wrapping flaps 1*b* and 1*c* on the both sides are folded back so that the underbelly is enveloped. In this embodiment, first, the wrapping flap 1*c* on the left side is folded back onto the bottom flap 1*a* applied on the underbelly, then the hook-and loop fastener 1*cif* on the inner surface of the wrapping flap 1*c* on the left side is fastened to the hook-and-loop fastener 1*af* on the outer surface of the bottom flap 1*a*; further, the wrapping flap 1*b* on the right side is folded back onto the wrapping flap 1*c* on the left side applied on the underbelly, and the hook-and-loop fastener 1*bf* on the inner surface of the wrapping flap 1*b* on the right side is fastened to the hook-and loop fastener 1*cf* on the outer surface of the wrapping flap 1*c* on the left side to complete putting on the diaper cover 1.

When sliding the diaper cover 1 under the buttocks of the bedridden aged or sick person in the preparatory steps stated above, the defecation tube 2*b* of the feces receiver 2, the tube protruding pendently from the opening for defecation and urination 1*h*, should be inserted at the same time in the defecation hole 10*h* that opens roughly in the center of the bed 10.

Figure 7:
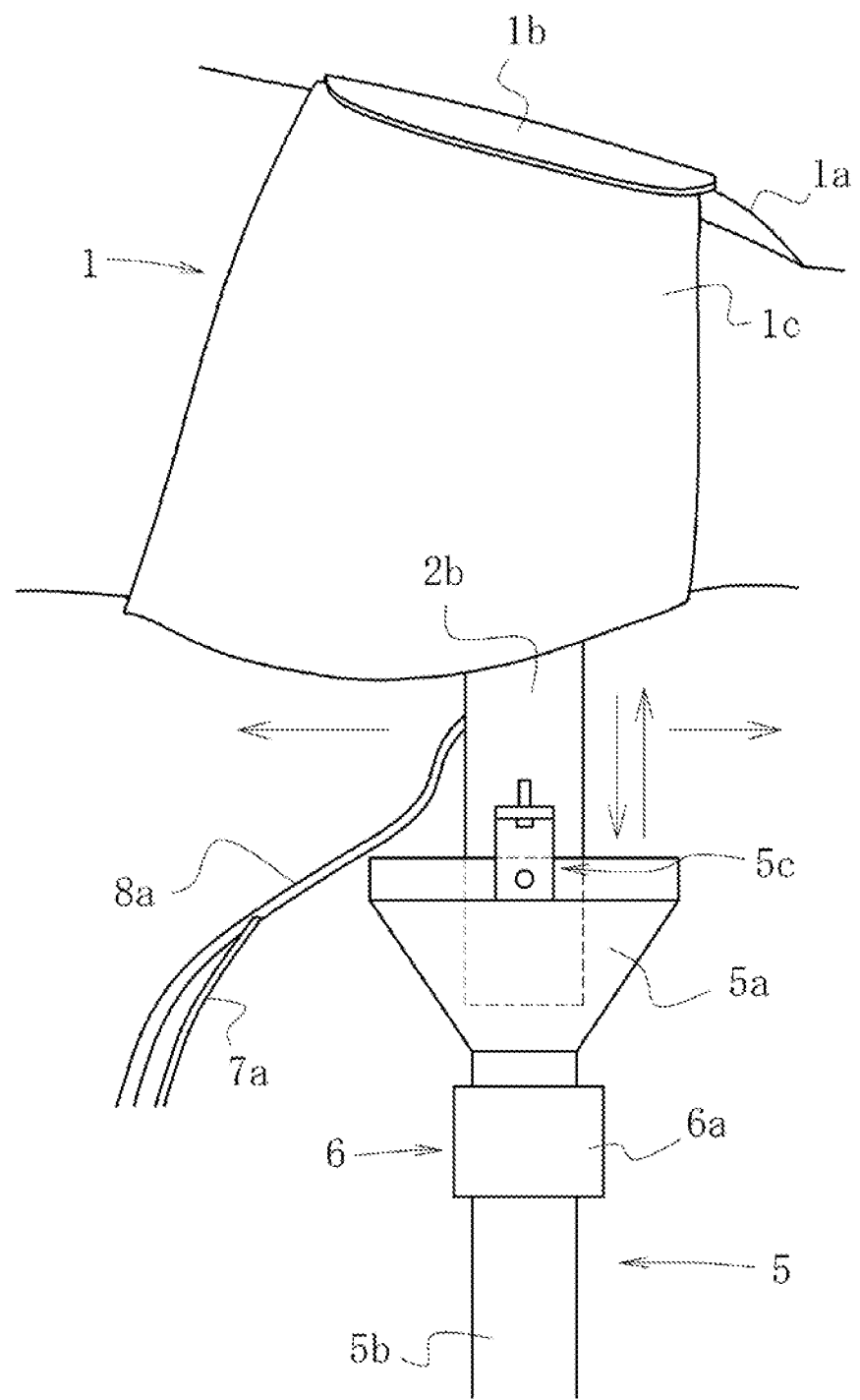
FIG. 7 This is an explanatory side view schematically illustrating a state of the drop-type automatic excrement processing device in the embodiment in which the defection tube of the feces receiver protruding downward from the diaper cover is inserted in the funnel-shaped part of the feces and urine intake pipe in a manner that allows a free relative movement in raising and lowering and in a slanting and upright-raising.

Meanwhile, the other components of this drop-type automatic excrement processing device should be installed under the objective bed 10 in advance. As shown in FIG. 8, the wastes container 4, the washing-water tank 7, the warm wind generating means 8 on the washing-water tank 7, and the control means 9 on the wastes container 4 are placed under the bed 10. The funnel-shaped part 5a of the upper part of the feces and urine intake pipe 5 risen from the wastes container 4 is fixed on the undersurface of the bed 10 using the pair of the L-shaped connection metal fittings 5c as stated above. The funnel-shaped part 5a is fitted on the bed 10 using the L-shaped connection metal fittings 5c, as shown in FIGS. 7, 8, and 10, mutually aligning the axes of the funnel-shaped part 5a and the defecation hole 10h of the bed 10 in a manner that allows relative slanting with respect to the longitudinal direction of the bed 10.

Thus, under this situation, the defecation tube 2b inserted in the defecation hole 10h in the bed 10 becomes in a state of being inserted in the funnel-shaped part 5a on the uppermost part of the feces and urine intake pipe 5, with free relative movements in raising and lowering and in slanting allowed. The blower tube 8a and the water pipe 7a are draw out below the bed 10 through the defection hole 10h in the bed 10, wherein the top end of blower tube 8a is connected to the upper-intermediate part of the defecation tube 2b and the water pipe 7a is inserted in the blower tube 8a at the upper-intermediate part thereof and is extended to near the uppermost end of the defecation tube 2b through inside the blower tube 8a. The connector 8a1 on the bottom end of the upper part of the blower tube 8a is connected to the connector 8a2 on the uppermost end of the lower part of the blower tube 8a so that the blower tube 8a is connected to the warm wind generating means 8. The connector 7a1 on one end on the bottom end of the upper part of the water pipe 7a is connected to the connector 7a2 on the other end on the upper end of the lower part of the water pipe 7a so that the water pipe 7a is connected to the washing-water tank 7 through the pump unit 7p.

The drop-type automatic excrement processing device in use works as follows. When the bedridden aged or sick person, who wears the diaper cover 1 having the feces receiver 2 or other components thereon, defecates or urinates, the excrement falls into the funnel-shaped part 5a of the upper part of the feces and urine intake pipe 5 through the defecation tube 2b of the feces receiver 2 in the diaper cover 1. The excrement falling into that part slips down from there to reach the valve unit 6 provided on the upper-intermediate part of the straight pipe part 5b located below the feces and urine intake pipe 5 and the matter drops on the valve member 6b. When the excrement drops on the valve member 6b of the valve unit 6, the valve member 6b rotates downward due to the weight of the excrement on it. The excrement on the valve member 6b then falls down through the straight pipe part 5b below the valve unit 6 and is collected in the wastes container 4. Excrement in continuation is also collected in the wastes container 4 going through the same process as the above.

When the excrement drops on the valve member 6b of the valve unit 6 and the valve member 6b rotates downward by more than a predetermined angle, that rotation is detected by a detection means, which is not illustrated. The detection signal issued by that detection means enters the control means 9. One minute and 30 seconds after the signal entering, the control means 9 sends a pump-driving signal to the pump unit 7p in the washing-water tank 7. Thereby, the control means 9 makes the pump unit 7p operate a pumping action of feeding 300 cc of washing-water in 10 seconds. With this pumping action, the warm washing-water in the washing-water tank 7 is sent to the buttocks, which is covered with the diaper cover 1, of the bedridden aged or sick person through the water pipe 7a and is jetted from the top end of the water pipe 7a to the buttocks. The washing-water in the washing-water tank 7 is always warmed to the predetermined temperature by the warming unit. The jetting is applied for 10 seconds as stated above and the buttocks is cleaned. The washing-water after use is collected also in the wastes container 4 flowing through the similar path to that for the excrement.

After the washing of 10 seconds, the control means 9 sends a signal to the warm wind generating means 8 to drive for two minutes. Thereby, the warm wind generated by a blower and a heating means is fed to the buttocks, which is covered with the diaper cover 1, of the bedridden aged or sick person through the blower tube 8a to dry the buttocks.

While the pumping action of the pump unit 7p in the washing-water tank 7 or the warm wind feeding action of the warm wind generating means 8 is in operation, the detection signal in detection of excrement outputted from the valve member 6 is ignored. Thereby, an unnecessary repetition of above-stated operating cycle caused by a detection signal generated from the valve unit 6 attributable to the flowing-down of the warm washing-water is avoided.

As stated above, the inside of the diaper cover 1 is washed with warm washing-water and dried with warm wind immediately when the defecation or urination is detected by the valve unit 6 provided in the upper-intermediate part of the feces and urine intake pipe 5. Therefore, the buttocks and loins of the bedridden aged or sick person, who is the wearer of the device, as well as the feces receiver 2, etc. inside the diaper cover 1, are always maintained in a sanitary and dry condition.

During these actions stated above, a mixture of the filth and washing-water flows down into the wastes container 4, causing the pushing out of the gas staying in the upper part of the container from the exhaust port 4a. The drying wind also passes through this container and is exhausted into air from the exhaust port 4a. In this exhaust, such gases are released with bad smell components removed by the filter in the exhaust port 4a; there is therefore no possibility of spreading the bad smell outside.

As stated above, the defecation tube 2b of the feces receiver 2 protruding pendently from the undersurface of the diaper cover 1 is inserted in the funnel-shaped part 5a of the upper part of the feces and urine intake pipe 5 risen from the wastes container 4, with free relative movement in raising and lowering and in slanting allowed. Even if the bedridden aged or sick person who wears the diaper cover 1 moves due to various reasons, the connection relation between the defecation tube 2b and the funnel-shaped part 5a can adapt freely to such movement; no troubles therefore will happen. The bedridden aged or sick person wearing the diaper cover 1 can move freely to some extent, wearing it on.

INDUSTRIAL APPLICABILITY

The drop-type automatic excrement processing device by the present invention is usable in the fields of welfare device manufacturing and similar fields.

DESCRIPTION OF REFERENCE NUMERALS

1 Diaper cover
1a Bottom flap
1af Hook-and-loop fastener on outer surface of bottom flap
1aif Hook-and-loop fastener on inner surface of bottom flap
1b Wrapping flap (on the right side)
1bf Hook-and-loop fastener on wrapping flap (right side)

1*c* Wrapping flap (on the left side)
1*cf* Hook-and-loop fastener on outer surface of wrapping flap (on the left side)
1*cif* Hook-and-loop fastener on inner surface of wrapping flap (on the left side)
1*h* Opening for defecation and urination
2 Feces receiver
2*a* Belt-shaped rubber sheet part
2*a*1 Round end
2*a*2 Circular opening
2*af* Hook-and-loop fastener on belt-shaped rubber sheet part
2*b* Defecation tube
2*b*1 Opening edge
3 Urine catching pad
3*a* Opening
4 Wastes container
4*a* Exhaust port
5 Feces and urine intake pipe
5*a* Funnel-shaped part
5*b* Straight pipe part
5*c* L-shaped connection metal fitting
5*c*1 Vertical tongue
5*c*2 Horizontal tongue
6 Valve unit
6*a* Valve box
6*b* Valve member
7 Washing-water tank
7*a* Water pipe
7*a*1 Connector on one side
7*a*11 Gripping sleeve of connector on one side
7*a*12 Annular magnet of connector on one side
7*a*2 Connector on the other side
7*a*21 Gripping sleeve of connector on the other side
7*a*22 Annular magnet of connector on the other side
7*p* Pump unit
8 Warm wind generating means
8*a* Blower tube
8*a*1 Connector on bottom end of upper part of blower tube
8*a*2 Connector on top end of lower part of blower tube
9 Control means
10 Bed
10*h* Defecation hole

The invention claimed is:

1. A drop-type automatic excrement processing device, comprising:
a diaper cover having an opening for defecation and urination configured to be positioned at a buttocks-corresponding position of a user;
a feces receiver including a belt-shaped rubber sheet part to be arranged inside said diaper cover, one end of said belt-shaped rubber sheet part being circular and having a circular opening, a defecation tube, an opening edge of a top end of which being fixedly jointed to an opening edge of the circular opening of the circular end of said belt-shaped rubber sheet part, a blower tube communicating with upper-inside area of said defecation tube, and a water pipe inserted in an intermediate part of said blower tube, a top end of said water pipe protruding toward said belt-shaped rubber sheet part from said defecation tube;
a disposable urine catching pad arranged between said belt-shaped rubber sheet part of said feces receiver and an inside of said diaper cover in such a state that said defecation tube is inserted in said opening for defecation and urination of said diaper cover from the inside thereof and said belt-shaped rubber sheet part is arranged on a lower part of the inside of said diaper cover;
a feces and urine intake pipe, the bottom end of which being connected to a wastes container, said defecation tube being adapted to insert into a funnel-shaped upper part of said feces and urine intake pipe, wherein the funnel-shaped upper part allows slant-insertion and free movement in raising and lowering of the defecation tube, said defecation tube being pendent downward below a bed through a defecation hole in said bed on which the user lies, said funnel-shaped part being fitted on an undersurface of said bed;
a valve unit inserted in an intermediate part of said feces and urine intake pipe, said valve unit being opened detecting the occurrence of defecation and urination based on weight or pressure caused by washing-water, exhaust air, or feces or urine from the user;
a washing-water tank connected to said water pipe through a pump unit, said washing-water tank having a warming unit;
a warm wind generating means connected to said blower tube; and
a control means that controls said pump unit and said warm wind generating means so that, when said valve unit opens while said pump unit or said warm wind generating means is not operating, said pump unit feeds a predetermined quantity of warm washing-water into said water pipe after a predetermined time after the opening of said valve unit and said warm wind generating means blows warm wind into said blower tube for a predetermined time, after the water feeding stops.

2. A drop-type automatic excrement processing device according to claim 1,
wherein an upper end of said funnel-shaped part of said feces and urine intake pipe is fitted on the undersurface of said bed in a manner that allows relative slanting with respect to said bed so that said funnel-shaped upper part keeps a horizontal position when said bed is raised.

3. A drop-type automatic excrement processing device according to claim 1,
wherein said water pipe comprises first and second segments joined together by a connector,
wherein said connector has first and second portions,
wherein said first portion comprises a gripping sleeve and an annular magnet positioned inside said gripping sleeve, said annular magnet having a recessed end being recessed by a predetermined distance from a leading end of the gripping sleeve, said first segment of said water pipe penetrates through said annular magnet and protrudes beyond said recessed end of the annular magnet by a penetration distance, and
wherein said second portion of the connector comprises a second gripping sleeve and a reversed polarity annular magnet positioned inside said second gripping sleeve, said reversed polarity annular magnet has a protruding end that protrudes by said predetermined distance from one end of said second gripping sleeve, said second segment of said water pipe penetrates through an opening in said reversed polarity annular magnet and is recessed by said penetration distance from said protruding end of the reversed polarity annular magnet.

* * * * *